US011807861B2

(12) United States Patent
Gilbertson et al.

(10) Patent No.: US 11,807,861 B2
(45) Date of Patent: *Nov. 7, 2023

(54) METHODS AND COMPOSITIONS FOR EXPRESSION OF TRANSGENES IN PLANTS

(71) Applicant: Monsanto Technology LLC, St. Louis, MO (US)

(72) Inventors: Larry Gilbertson, Chesterfield, MO (US); Jon Lamb, Wildwood, MO (US); Jason Ward, St. Peters, MO (US); Jianping Xu, Chesterfield, MO (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 22 days.

This patent is subject to a terminal disclaimer.

(21) Appl. No.: 17/469,487

(22) Filed: Sep. 8, 2021

(65) Prior Publication Data

US 2022/0064659 A1    Mar. 3, 2022

Related U.S. Application Data

(63) Continuation of application No. 16/221,346, filed on Dec. 14, 2018, now Pat. No. 11,162,109, which is a continuation of application No. 14/516,483, filed on Oct. 16, 2014, now Pat. No. 10,179,916, which is a continuation of application No. 12/910,377, filed on Oct. 22, 2010, now Pat. No. 8,937,214.

(60) Provisional application No. 61/254,586, filed on Oct. 23, 2009.

(51) Int. Cl.
*C12N 15/82* (2006.01)

(52) U.S. Cl.
CPC ..... *C12N 15/8261* (2013.01); *C12N 15/8201* (2013.01); *C12N 15/8205* (2013.01); *C12N 15/8216* (2013.01)

(58) Field of Classification Search
CPC .................................................. C12N 15/82
See application file for complete search history.

(56) References Cited

U.S. PATENT DOCUMENTS

| | | | | |
|---|---|---|---|---|
| 6,187,994 B1* | 2/2001 | Baszczynski | .......... | C12N 15/90 800/298 |
| 6,448,473 B1* | 9/2002 | Mitsky | ............... | C12N 15/8243 800/278 |
| 6,713,259 B2* | 3/2004 | Levine | ............... | C12N 15/8271 435/6.15 |
| 7,129,392 B2* | 10/2006 | Hahn | ................. | C12N 15/8243 435/468 |
| 8,937,214 B2 | 1/2015 | Gilbertson | | |

FOREIGN PATENT DOCUMENTS

WO    WO 2008/063755    5/2008
WO    WO 2011/088299    7/2011

OTHER PUBLICATIONS

Chen et al. Theoretical and Applied Genetics vol. 99, pp. 755-760 (Year: 1999).*
Chen et al. Plant Molecular Biology vol. 62, pp. 927-936 (Year: 2006).*
Wang et al. Chinese Science Bulletin vol. 44, No. 22, pp. 2051-2058 (Year: 1999).*
Chen et al., "Development of wheat scab symptoms is delayed in transgenic wheat plants that constitutively express a rice thaumatin-like protein gene," *Theor Appl Genet* 99:755- 760; 1999.
Chen et al., "A gateway-based platform for multigene plant transformation," *Plant Mol. Biol.*, 62(6):927-936, 2006.
Chen et al., "Expression and inheritance of multiple transgenes in rice plants," *Nature Biotech.*, 16:1060-1064, 1998.
Dafny-Yelin et al., "Delivery of multiple transgenes to plant cells," *Plant Physiol.*, 145(4):1118-1128, 2007.
Fu et al., "Linear transgene constructs lacking vector backbone sequences generate low-copy-number transgenic plants with simple integration patterns," *Tansgenic Res.*, 9(1):11-19, 2000.
Halpin, "Gene stacking in transgenic plants - the challenge for $21^{st}$ century plant biotechnology," *Plant Biotech. J.*, 3:141-155, 2005.
Maqbool et al., "Expression of multiple insecticidal genes confers broad resistance against a range of different rice pests," *Molecular Breed.*, 7(1):85-93, 2001.
PCT International Search Report regarding Application No. PCT/US2010/053756, dated Jan. 28, 2011.
Que et al., "Trait stacking in transgenic crops," *GM Crops* 1:4, pp. 220-229; Jul./Aug./Sept./Oct. 2010.
Wang et al. Expression of two insect-resistant genes crylA (B&C) / GNA in transgenic tobacco plants results in added protection against both cotton bollworm and aphids *Chinese Science Bulletin* 44(22):2051-2058; 1999.

* cited by examiner

*Primary Examiner* — David H Kruse
(74) *Attorney, Agent, or Firm* — DENTONS US LLP; Paula Degrandis

(57) ABSTRACT

Transgenic plants are provided comprising a plurality of transgenes comprised in a single locus. In certain aspects, 7 or more transgenes may be expressed from a first locus. Methods are provided for transformation of plant cells with a plurality of transgenes. Also provided are methods for expressing and enhancing the expression of one or more transgenes in a plant.

22 Claims, 6 Drawing Sheets

METHODS AND COMPOSITIONS FOR EXPRESSION OF TRANSGENES IN PLANTS

This application is a continuation of U.S. application Ser. No. 16/221,346, filed Dec. 14, 2018, which is a continuation of U.S. application Ser. No. 14/516,483, filed Oct. 16, 2014, now U.S. Pat. No. 10,179,916; which is a continuation of U.S. application Ser. No. 12/910,377, filed Oct. 22, 2010, now U.S. Pat. No. 8,937,214; which claims the priority of U.S. Provisional Application No. 61/254,586, filed Oct. 23, 2009, the entire disclosures of which are incorporated herein by reference.

BACKGROUND OF THE INVENTION

Field of the Invention

The invention relates to the field of molecular biology. More specifically, the invention relates to transgenic plants comprising multiple transgenes and methods for expressing a plurality of transgenes in plants.

Description of the Related Art

One of the goals of genetic engineering is to produce hosts, such as plants, with important characteristics or traits. Recent advances in genetic engineering have provided the requisite tools to transform hosts to contain and express foreign genes. Particularly desirable traits of interest for genetic engineering would include but are not limited to protein production, resistance to insects and other pests and disease-causing agents, tolerances to herbicides, enhanced stability, yield, or shelf-life, environmental tolerances, and nutritional enhancements.

The technological advances in transformation and regeneration have enabled researchers to take segments of DNA, such as a gene or genes from a heterologous source, or native source and incorporate the exogenous DNA into a host's genome. The gene or gene(s) can then be expressed in the host cell to exhibit the added characteristic(s) or trait(s). In most transformation approaches, a single vector containing 1-2 genes conferring desirable characteristic(s) is introduced into a host of interest via an appropriate expression vector. Expression of a greater number of transgenes in host cells and organisms has proven to be costly and time consuming.

SUMMARY OF THE INVENTION

In a first aspect, there is provided a transgenic plant comprising a first locus comprising a plurality of transgenes operably linked to promoter sequences. For example, a locus may comprise a plurality of expression cassettes for the expression of a plurality of transgenes. In certain embodiments, a first locus comprises at least 6, at least 7, at least 8, at least 9, at least 10, or more, transgenes.

In certain aspects, a transgenic plant according to the invention comprises enhanced expression of at least one transgene relative to an otherwise isogenic transgenic plant wherein the same transgene is introduced in a locus comprising fewer total transgenes than a locus in a plant according to the invention. In further embodiments, a plant according to the invention comprises enhanced expression of at least 2, 3, 4, 5 or more transgenes relative to a second, otherwise isogenic, transgenic plant wherein the corresponding transgenes are comprised in a locus in the second plant that comprises fewer total transgenes than a plant according to the invention.

In further aspects, a plant according to the invention comprises a first locus comprising a plurality of transgenes wherein at least 1, 2, 3, 4, 5, 6, 7, 8, 9 or more of the transgenes confers a trait of agronomic interest when expressed in a plant. For example, a transgene may confer herbicide tolerance (e.g., glyphosate or other herbicide tolerance), drought resistance, insect resistance, fungus resistance, virus resistance, bacteria resistance, male sterility, cold tolerance, salt tolerance, increased yield, enhanced oil composition, increased oil content, enhanced nutrient use efficiency or altered amino acid content to a plant expressing the transgene. In certain embodiments, a first locus comprises a plurality of transgenes that confer traits of agronomic interest. For example, a first locus may comprise at least one transgene that confers herbicide tolerance, at least one transgene that confers insect resistance and/or at least one transgene that confers drought tolerance. In a further embodiment, a first locus comprises at least two transgenes that confer herbicide tolerance, at least two transgenes that confer insect resistance and/or at least two transgenes that confer drought tolerance. In still a further embodiment, a first locus comprises at least one transgene that confers above-ground insect resistance and at least one transgene that confers below-ground insect resistance.

A variety of transgenes are known in art and may be used in accordance with the invention. For example, one or more transgenes may be selected from those disclosed in International (PCT) Publn. WO 2008/063755, the contents of which are incorporated herein by reference in their entirety. Examples, of transgenes for use according to the invention include, but are not limited to, transgenes conferring herbicide tolerance, drought tolerance or insect tolerance.

In further aspects, a transgenic plant according to the invention is a monocotyledonous plant such as, wheat, maize, rye, rice, corn, oat, barley, turfgrass, sorghum, millet or sugarcane. In certain other embodiments, a transgenic plant is a dicotyledonous plant, such as tobacco, tomato, potato, soybean, cotton, canola, sunflower or alfalfa.

In certain aspects, the invention provides a part of a transgenic plant described herein, such as a protoplast, cell, gamete, meristem, root, pistil, anther, flower, seed, embryo, stalk or petiole. In certain embodiments, seed of a transgenic plant described herein is provided wherein the seed comprises the first locus comprising a plurality of transgenes. In a further embodiment, there is provided a progeny plant of a transgenic plant according to the invention wherein the progeny plant comprises the first locus comprising a plurality of transgenes. In still a further embodiment, there is provided a method for producing a commercial product comprising obtaining a plant according to the invention or part thereof and producing a commercial product therefrom.

In a further aspect, the invention provides a tissue culture of regenerable cells of a transgenic plant according to the invention. For example, the regenerable cells may be from embryos, meristematic cells, pollen, leaves, roots, root tips, anther, pistil, flower, seed, boll or stem. In still a further embodiment, there is provided a plant regenerated from the a tissue culture according to the invention.

In still a further aspect, there is provided a method of transforming a plant cell comprising introducing a plurality of transgenes into a plant cell, wherein the plurality of transgene are comprised on a single DNA molecule. For example, a transformation method may comprise introducing at least 6, 7, 8, 9 or 10 transgenes into a plant cell wherein the transgenes are comprised on a single DNA molecule. In a further embodiment, a transformation method comprises selecting a transformed plant cell wherein said cell comprises the plurality of transgenes in a single-copy transformation event (e.g., a transformation event that is free from backbone vector sequence).

In yet a further aspect, there is provided a method for expressing a plurality of transgenes in a plant comprising expressing said plurality of transgenes in the plant wherein the transgenes are comprised in a single locus said event comprising a plurality transgenes operably linked to promoter sequences.

In a further aspect, there is provided a method for enhancing the expression of at least a first transgene in a plant comprising expressing the transgene in the plant according to the invention. For example, transgene expression may be enhanced by expressing a transgene comprised in a locus wherein the locus comprises a plurality of additional transgenes. In certain embodiments, a plant comprises at least 5, 6, 7, 8, 9 or 10 additional transgenes. In a further embodiment, a method for enhancing expression of at least one transgene comprises enhancing expression of the transgene relative to an otherwise isogenic plant wherein the transgene is comprised in a locus that comprises fewer transgenes than the locus in a plant according to the invention. For example, an expressed transgene may be comprised in a locus comprising at least 5, 6, 7, 8 or 9 additional transgenes and its expression enhanced relative to expression of the same transgene from an otherwise isogenic plant comprising a locus with fewer additional transgenes (e.g., less than 5, 6, 7, 8 or 9 additional transgenes).

In still further aspects, a method for enhancing expression of at least one transgene in a plant transformed to contain a plurality of transgenes comprises enhancing expression of a transgene that confers herbicide tolerance, drought tolerance or insect tolerance. In still further embodiments, a method according to the invention may be defined as a method of enhancing the expression of two or more transgenes wherein the transgenes are comprised in a first transgenic event comprising a plurality of additional transgenes.

In certain aspects, two or more transgenes (e.g., a plurality of transgenes) are arranged in tandem. In one embodiment, tandem refers to an arrangement in which there is a substantial absence of intervening DNA between transgenes. In specific embodiments, tandem refers to lack of a length of intervening sequence that, if present, interferes with transgene expression and/or the ability to transform a plurality of transgenes into plants.

As used herein the terms "encode" or "encoding" with reference to a nucleic acid are used to make the invention readily understandable by the skilled artisan however these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein:

FIG. 1A, illustrates the binary T-DNA vector used for recombination in vector construction. FIG. 1B, provides a schematic of the 10 gene expression cassette.

DETAILED DESCRIPTION OF THE INVENTION

Figure 1A:
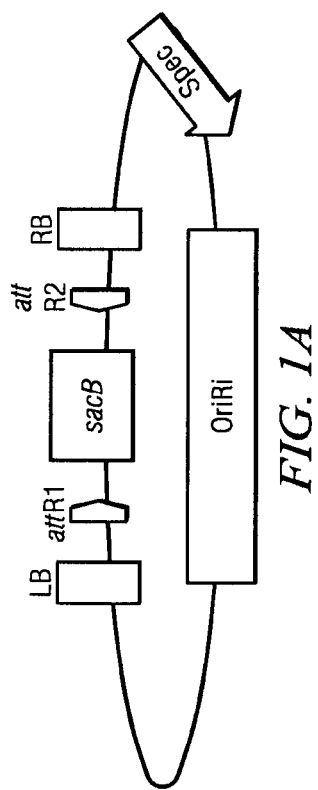
FIG. 1A-B: Vector schematics.

In certain aspects, the invention provides methods and compositions related to expression of multiple transgenes in plants from a single locus. For example, there is provided a method of transforming a plant cell with a vector comprising a plurality of transgenes and regenerating a plant therefrom. In another aspect, transgenic plants are provided that comprise a first locus comprising a plurality of transgenes linked to expression control sequences. In certain aspects, there is provided a method for expression of a plurality of transgenes in a transgenic plant comprising expressing a plurality of transgenes from a first locus comprising a plurality of transgenes linked to expression control sequences. In still a further aspect, there is provided a method for enhancing expression of one or more transgenes comprising expressing said one or more transgenes from a first locus comprising a plurality of transgenes.

In certain aspects, methods and plants according to the invention concern expression of plurality of transgenes comprised in a single locus that confer a plurality of traits of agronomic interest. In one embodiment, a locus comprises one or more transgenes that confer a herbicide tolerance trait and three or more transgenes that confer insect resistance traits. In another embodiment, a locus comprises one or more transgenes that confer a herbicide tolerance trait, two or more of the insect resistance traits, and one or more transgenes that confer a drought tolerance trait.

In still another aspect a locus comprises a transgene that confers male sterility. For example, a locus may comprise one or more transgenes that confer a herbicide tolerance trait, two or more transgenes that confer insect resistance traits, one or more transgenes that confer a drought tolerance trait, and one or more transgenes that confer a male sterility trait. In another embodiment, a locus comprises one or more transgenes that confer a herbicide tolerance trait, two or more transgenes that confer insect resistance traits, one or more transgenes that confer an enhanced amino acid content trait, one or more transgenes that confer a drought tolerance trait, and one or more transgenes that confer a male sterility trait.

In a further aspect, a locus may comprise a transgene that confers an increased yield trait. For instance, a locus may comprise one or more transgenes that confer a herbicide tolerance trait, two or more transgenes that confer insect resistance traits, one or more transgenes that confer a drought tolerance trait, one or more transgenes that confer a male sterility trait, and one or more transgenes that confer an increased yield trait. In another embodiment, a locus comprises one or more transgenes that confer herbicide tolerance trait, one or more transgenes that confer an insect resistance trait, one or more transgenes that confer an enhanced amino acid content trait, one or more transgenes that confer a drought tolerance trait, one or more transgenes that confer a male sterility trait, and one or more transgenes that confer an enhanced yield trait.

In still a further aspect, a locus may comprise a transgene that confers a nutrient use efficiency trait. For example, a locus may comprise one or more transgenes that confer a herbicide tolerance trait, two or more transgenes that confer insect resistance traits, one or more transgenes that confer drought tolerance traits, one or more transgenes that confer a the male sterility trait, one or more transgenes that confer an enhanced yield trait, and one or more transgenes that confer a nutrient use efficiency trait.

In yet further aspects, a locus may comprise a transgene that confers a cold tolerance trait. In one example, a locus may comprise one or more transgenes that confer a herbicide tolerance trait, two or more transgenes that confer insect resistance traits, one or more transgenes that confer a drought tolerance trait, one or more transgenes that confer a male sterility trait, one or more transgenes that confer an enhanced yield trait, one or more transgenes that confer a nutrient use efficiency trait and one or more transgenes that confer a cold tolerance trait. In another embodiment, a locus comprises one or more transgenes that confer a herbicide tolerance trait, one or more transgenes that confer an insect resistance trait, one or more transgenes that confer an enhanced amino acid content trait, one or more transgenes that confer a drought tolerance trait, one or more transgenes that confer a male sterility trait, one or more transgenes that confer an enhanced yield trait, one or more transgenes that confer a nutrient use efficiency trait, one or more transgenes that confer an enhanced oil content trait, one or more transgenes that confer an enhanced protein content trait, and one or more transgenes that confer a cold tolerance trait.

In certain aspects, a locus may comprise a transgene that confers an enhanced amino acid content trait. In another embodiment, a locus comprises one or more transgenes that confer a herbicide tolerance trait, three or more transgenes that confer insect resistance traits, and one or more transgenes that confer an enhanced amino acid content. In another embodiment, a locus comprises one or more transgenes that confer a herbicide tolerance trait, two or more transgenes that confer insect resistance traits, one or more transgenes that confer an enhanced amino acid content trait, and one or more transgenes that confer a drought tolerance trait.

In further aspects, a locus may comprise a transgene that confers an enhanced oil content trait. For example, a locus may comprise one or more transgenes that confer a herbicide tolerance trait, two or more transgenes that confer insect resistance traits, one or more transgenes that confer an enhanced amino acid content trait, one or more transgenes that confer a drought tolerance trait, one or more transgenes that confer a male sterility trait, one or more transgenes that confer an enhanced yield trait, and one or more transgenes that confer an enhanced oil content trait. In another embodiment, a locus comprises one or more transgenes that confer a herbicide tolerance trait, two or more transgenes that confer insect resistance traits, one or more transgenes that confer an enhanced amino acid content trait, one or more transgenes that confer a drought tolerance trait, one or more transgenes that confer a male sterility trait, one or more transgenes that confer an enhanced yield trait, one or more transgenes that confer a nutrient use efficiency trait, one or more transgenes that confer an enhanced oil content trait, one or more transgenes that confer an enhanced protein content trait, and one or more transgenes that confer a cold tolerance trait.

I. PLANT TRANSFORMATION AND TRANSGENE EXPRESSION CONSTRUCTS

Certain embodiments of the current invention concern plant transformation constructs. In certain embodiments of the invention, transgene coding sequences are provided operably linked to a promoter (e.g., a heterologous promoter), in either sense or antisense orientation. Expression constructs are also provided comprising these sequences, as are plants and plant cells transformed with the sequences.

The construction of vectors which may be employed in conjunction with plant transformation techniques using these or other sequences according to the invention will be known to those of skill of the art in light of the present disclosure (see, for example, Sambrook et al., 1989; Gelvin et al., 1990). The techniques of the current invention are thus not limited to any particular nucleic acid sequences.

Particularly useful for transformation are expression cassettes which have been isolated from such vectors. DNA segments used for transforming plant cells will, of course, generally comprise the RNA coding sequence, cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. However, this may not always be the case, and the present invention also encompasses transgenic plants incorporating non-expressed transgenes. Preferred components likely to be included with vectors used in the current invention are as follows.

A. Regulatory Elements

Exemplary promoters for expression of a transgene include plant promoter such as the CaMV 35S promoter (Odell et al., 1985), or others such as CaMV 19S (Lawton et al., 1987), nos (Ebert et al., 1987), Adh (Walker et al., 1987), sucrose synthase (Yang and Russell, 1990), a-tubulin, actin (Wang et al., 1992), cab (Sullivan et al., 1989), PEPCase (Hudspeth and Grula, 1989) or those associated with the R gene complex (Chandler et al., 1989). Tissue specific promoters such as root cell promoters (Conkling et al., 1990) and tissue specific enhancers (Fromm et al., 1986) are also contemplated to be particularly useful, as are inducible promoters such as ABA- and turgor-inducible promoters. In certain aspects, a promoter for use according to the invention is a ePCISV, TubA, eFMV, FMV, e35S, 35S or Ract1 promoter.

In certain aspects, transformation events comprised in transgenic plants according to the invention comprise a plurality of promoter sequences. In certain aspects, a promoter sequence is repeated no more than about 2, 3, 4, or 5 times in a single transformation event. In other embodiments, identical or highly homologous promoter sequences are linked to at least 2, 3, 4, 5 or more transgenes in a single transformation event. In certain embodiments, a transformation event comprising a plurality of transgenes comprises at least 2, 3, 4, 5, 6, 7, 8, 9 or 10 different promoter sequences.

In further embodiments, identical or highly homologous promoter sequences are linked to transgenes that confer similar traits (e.g., transgenes that confer insect resistance). In certain aspects, two or more identical or highly homologous promoter sequences are separated by at least 1, 2 or 3 expression cassettes within a single transformation event. In other embodiments, identical or highly homologous promoter sequences are linked to two or more contiguous expression cassettes in a single transformation event.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

It is specifically envisioned that transgene coding sequences may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue; a truncated (−90 to +8) 35S promoter which directs enhanced expression in roots, and an α-tubulin gene that also directs expression in roots.

B. Terminators

Transformation constructs prepared in accordance with the invention will typically include a 3' end DNA sequence that acts as a signal to terminate transcription and allow for the poly-adenylation of the mRNA produced by coding sequences operably linked to a transgene. Terminators which are deemed to be particularly useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired. In certain aspects, a terminator for use according to the invention is a Hsp17, TubA, Ara5, 35S, nos or Tr7 terminator.

In certain aspects, transformation events comprised in transgenic plants according to the invention comprise a plurality of terminator sequences. In certain aspects, a terminator sequence is repeated no more than about 2, 3, 4, or 5 times in a single transformation event. In other embodiments, identical or highly homologous terminator sequences are linked to at least 2, 3, 4, 5 or more transgenes in a single transformation event. In certain embodiments, a transformation event comprising a plurality of transgenes comprises at least 2, 3, 4, 5, 6, 7, 8, 9 or 10 different terminator sequences.

In further embodiments, identical or highly homologous terminator sequences are linked to transgenes that confer similar traits (e.g., transgenes that confer insect resistance). In certain aspects, two or more identical or highly homologous terminator sequences are separated by at least 1, 2 or 3 expression cassettes with a single transformation event. In other embodiments, identical or highly homologous terminator sequences are linked to two or more contiguous expression cassettes in a single transformation event.

C. Intron Sequences

In certain aspects, intron sequences are included an expression cassette and may enhance transgene expression. In certain aspects, an intron for use according to the invention is a Ract1, TubA, Sus1 or Hsp70 intron.

In certain aspects, transformation events comprised in transgenic plants according to the invention comprise a plurality of intron sequences. In certain aspects, an intron sequence is repeated no more than about 2, 3, 4, or 5 times in a single transformation event. In other embodiments, identical or highly homologous intron sequences are linked to at least 2, 3, 4, 5 or more transgenes in a single transformation event. In certain embodiments, a transformation event comprising a plurality of transgenes comprises at least 2, 3, 4, 5, 6, 7, 8, 9 or 10 different intron sequences.

In further embodiments, identical or highly homologous intron sequences are linked to transgenes that confer similar traits (e.g., transgenes that confer insect resistance). In certain aspects, two or more identical or highly homologous intron sequences are separated by at least 1, 2 or 3 expression cassettes within a single transformation event. In other embodiments, identical or highly homologous intron sequences are linked to two or more contiguous expression cassettes in a single transformation event.

D. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

E. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms "selectable" or "screenable markers" also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154,204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; an aequorin gene (Prasher et al., 1985) which may be employed in calcium-sensitive bioluminescence detection; or a gene encoding for green fluorescent protein (Sheen et al., 1995; Haseloff et al., 1997; Reichel et al., 1996; Tian et al., 1997; WO 97/41228).

Another screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It also is envisioned that this system may be developed for population screening for bioluminescence, such as on tissue culture plates, or even for whole plant screening. The gene which encodes green fluorescent protein (GFP) is also contemplated as a particularly useful reporter gene (Sheen et al., 1995; Haseloff et al., 1997; Reichel et al., 1996; Tian et al., 1997; WO 97/41228). Expression of green fluorescent protein may be visualized in a cell or plant as fluorescence following illumination by particular wavelengths of light.

F. Example Transgenes

1. Male Sterility

Examples of genes conferring male sterility include those disclosed in U.S. Pat. Nos. 3,861,709, 3,710,511, 4,654,465, 5,625,132, and 4,727,219, each of the disclosures of which are specifically incorporated herein by reference in their entirety. The use of herbicide-inducible male sterility genes is described in U.S. Pat. No. 6,762,344. Male sterility genes can increase the efficiency with which hybrids are made, in that they eliminate the need to physically emasculate plants used as a female in a given cross.

2. Herbicide Tolerance

Numerous herbicide resistance genes are known and may be employed with the invention. An example is a gene conferring resistance to a herbicide that inhibits the growing point or meristem, such as an imidazalinone or a sulfonylurea. Exemplary genes in this category code for mutant ALS and AHAS enzyme as described, for example, by Lee et al., (1988); Gleen et al., (1992) and Miki et al., (1990).

Resistance genes for glyphosate (resistance conferred by mutant 5-enolpyruvl-3 phosphikimate synthase (EPSP) and aroA genes, respectively) and other phosphono compounds such as glufosinate (phosphinothricin acetyl transferase (PAT) and *Streptomyces hygroscopicus* phosphinothricin-acetyl transferase (bar) genes) may also be used. See, for example, U.S. Pat. No. 4,940,835 to Shah, et al., which discloses the nucleotide sequence of a form of EPSPS which can confer glyphosate resistance. Examples of specific EPSPS transformation events conferring glyphosate resistance are provided by U.S. Pat. No. 6,040,497.

A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyltransferase gene is provided in European application No. 0 242 246 to Leemans et al. DeGreef et al., (1989), describe the production of transgenic plants that express chimeric bar genes coding for phosphinothricin acetyl transferase activity. Exemplary of genes conferring resistance to phenoxy propionic acids and cycloshexones, such as sethoxydim and haloxyfop are the Acct-S1, Accl-S2 and Acct-S3 genes described by Marshall et al., (1992). In certain aspects, a DMO transgene may be used to mediate dicamba tolerance.

Genes are also known conferring resistance to a herbicide that inhibits photosynthesis, such as a triazine (psbA and gs+ genes) and a benzonitrile (nitrilase gene). Przibila et al., (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., (1992).

Other examples of herbicide resistance have been described, for instance, in U.S. Pat. Nos. 6,803,501; 6,448, 476; 6,248,876; 6,225,114; 6,107,549; 5,866,775; 5,804, 425; 5,633,435; 5,463,175.

3. Disease and Pest Resistance

Plant defenses are often activated by specific interaction between the product of a disease resistance gene (R) in the plant and the product of a corresponding avirulence (Avr) gene in the pathogen. A plant line can be transformed with cloned resistance gene to engineer plants that are resistant to specific pathogen strains. See, for example Jones et al., (1994) (cloning of the tomato Cf-9 gene for resistance to *Cladosporium fulvum*); Martin et al., (1993) (tomato Pto gene for resistance to *Pseudomonas syringae* pv.); and Mindrinos et al., (1994) (*Arabidopsis* RSP2 gene for resistance to *Pseudomonas syringae*).

A viral-invasive protein or a complex toxin derived therefrom may also be used for viral disease resistance. For example, the accumulation of viral coat proteins in transformed plant cells imparts resistance to viral infection and/or disease development effected by the virus from which the coat protein gene is derived, as well as by related viruses. See Beachy et al., (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

A virus-specific antibody may also be used. See, for example, Tavladoraki et al., (1993), who show that transgenic plants expressing recombinant antibody genes are protected from virus attack. Virus resistance has also been described in, for example, U.S. Pat. Nos. 6,617,496; 6,608, 241; 6,015,940; 6,013,864; 5,850,023 and 5,304,730.

Logemann et al., (1992), for example, disclose transgenic plants expressing a barley ribosome-inactivating gene have an increased resistance to fungal disease. Other examples of fungal disease resistance are provided in U.S. Pat. Nos. 6,653,280; 6,573,361; 6,506,962; 6,316,407; 6,215,048; 5,516,671; 5,773,696; 6,121,436; 6,316,407; and 6,506, 962).

Nematode resistance has been described, for example, in U.S. Pat. No. 6,228,992 and bacterial disease resistance in U.S. Pat. No. 5,516,671.

4. Insect Resistance

One example of an insect resistance gene includes a *Bacillus thuringiensis* protein, a derivative thereof or a synthetic polypeptide modeled thereon. See, for example, Geiser et al., (1986), who disclose the cloning and nucleotide sequence of a Bt δ-endotoxin gene. Moreover, DNA molecules encoding δ-endotoxin genes can be purchased from the American Type Culture Collection, Manassas, Va., for example, under ATCC Accession Nos. 40098, 67136, 31995 and 31998. Another example is a lectin. See, for example, Van Damme et al., (1994), who disclose the nucleotide sequences of several *Clivia miniata* mannose-binding lectin genes. A vitamin-binding protein may also be used, such as avidin. See PCT application US93/06487, the contents of which are hereby incorporated by reference. This application teaches the use of avidin and avidin homologues as larvicides against insect pests.

Yet another insect resistance gene is an enzyme inhibitor, for example, a protease or proteinase inhibitor or an amylase inhibitor. See, for example, Abe et al., (1987) (nucleotide sequence of rice cysteine proteinase inhibitor), Huub et al., (1993) (nucleotide sequence of cDNA encoding tobacco proteinase inhibitor I), and Sumitani et al., (1993) (nucleotide sequence of *Streptomyces nitrosporeus* α-amylase inhibitor). An insect-specific hormone or pheromone may also be used. See, for example, the disclosure by Hammock et al., (1990), of baculovirus expression of cloned juvenile hormone esterase, an inactivator of juvenile hormone.

Still further nucleic acids encoding proteins that confer insect resistance can be derived from a number of organisms that include, but are not limited to, *Bacillus thuringiensis*, Xenorhabdus sp., or *Photorhabdus* sp. For example, construct or transgenic plants may comprise one or more *B. thuringiensis* proteins toxic to an insect species or multiple insect species (e.g., Cry1Aa, Cry1Ab, Cry1Ac, Cry1Ba, CryBb, Cry1Ca, Cry1F, Cry2Aa, Cry2Ab, Cry3A, Cry3B, Cry3C, Cry9, Cry34 or Cry 35). Use of multiple genes to confer insect resistance may delay the onset of resistance in a population of an otherwise susceptible insect species to one or more of the insecticidal nucleic acids expressed within the transgenic plant. Alternatively, expression of a *B. thuringiensis* insecticidal protein toxic to a particular target insect pest along with a different proteinaceous agent toxic to the same insect pest but which confers toxicity by a means different from that exhibited by the *B. thuringiensis* toxin is desirable. Such other different proteinaceous agents may comprise any of Cry insecticidal proteins, Cyt insecticidal proteins, insecticidal proteins from Xenorhabdus sp. or *Photorhabdus* sp., *B. thuringiensis* vegetative insecticidal proteins, and the like. Examples of such proteins encoded by insect toxin genes includes, but are not limited to, ET29, TIC809, TIC810, TIC105, TIC127, TIC128, TIC812 and ET37 (WO 07/027776), TIC807, AXMI-027, AXMI-036, and AXMI-038 (WO 06/107761), AXMI-018, AXMI-020, and AXMI-021 (WO 06/083891), AXMI-010 (WO 05/038032), AXMI-003 (WO 05/021585), AXMI-008 (US 2004/0250311), AXMI-006 (US 2004/0216186), AXMI-007 (US 2004/0210965), AXMI-009 (US 2004/0210964), AXMI-014 (US 2004/0197917), AXMI-004 (US 2004/0197916), AXMI-028 and AXMI-029 (WO 06/119457) and AXMI-007, AXMI-008, AXMI-0080rf2, AXMI-009, AXMI-014 and AXMI-004 (WO 04/074462). All of the foregoing references are incorporated herein in their entirety.

Additional nucleic acids that can be used to confer insect resistance may encode RNA for gene suppression of an essential gene in the insect pest. For example, a nucleic acid may comprise an antisense or dsRNA sequence for suppression of an insect Dv49 gene.

Still other examples include an insect-specific antibody or an immunotoxin derived therefrom and a developmental-arrestive protein. See Taylor et al., (1994), who described enzymatic inactivation in transgenic tobacco via production of single-chain antibody fragments. Numerous other examples of insect resistance have been described. See, for example, U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245 and 5,763,241.

5. Modified Fatty Acid, Phytate and Carbohydrate Metabolism

Genes may be used conferring modified fatty acid metabolism, in terms of content and quality. For example, stearyl-ACP desaturase genes may be used. See Knutzon et al., (1992). Various fatty acid desaturases have also been described, such as a *Saccharomyces cerevisiae* OLE1 gene encoding Δ9-fatty acid desaturase, an enzyme which forms the monounsaturated palmitoleic (16:1) and oleic (18:1) fatty acids from palmitoyl (16:0) or stearoyl (18:0) CoA (McDonough et al., 1992); a gene encoding a stearoyl-acyl carrier protein delta-9 desaturase from castor (Fox et al. 1993); Δ6- and Δ12-desaturases from the cyanobacteria *Synechocystis* responsible for the conversion of linoleic acid (18:2) to gamma-linolenic acid (18:3 gamma) (Reddy et al. 1993); a gene from *Arabidopsis thaliana* that encodes an omega-3 desaturase (Arondel et al. 1992)); plant Δ9-desaturases (PCT Application Publ. No. WO 91/13972) and soybean and *Brassica* Δ15 desaturases (European Patent Application Publ. No. EP 0616644).

Modified oils production is disclosed, for example, in U.S. Pat. Nos. 6,444,876; 6,426,447 and 6,380,462. High oil production is disclosed, for example, in U.S. Pat. Nos. 6,495,739; 5,608,149; 6,483,008 and 6,476,295. Modified fatty acid content is disclosed, for example, in U.S. Pat. Nos. 6,828,475; 6,822,141; 6,770,465; 6,706,950; 6,660,849; 6,596,538; 6,589,767; 6,537,750; 6,489,461 and 6,459,018.

Phytate metabolism may also be modified by introduction of a phytase-encoding gene to enhance breakdown of phytate, adding more free phosphate to the transformed plant. For example, see Van Hartingsveldt et al., (1993), for a disclosure of the nucleotide sequence of an *Aspergillus niger* phytase gene. In corn, this, for example, could be accomplished by cloning and then reintroducing DNA associated with the single allele which is responsible for corn mutants characterized by low levels of phytic acid. See Raboy et al., (2000).

A number of genes are known that may be used to alter carbohydrate metabolism. For example, plants may be transformed with a gene coding for an enzyme that alters the branching pattern of starch. See Shiroza et al., (1988) (nucleotide sequence of *Streptococcus* mutants fructosyl-transferase gene), Steinmetz et al., (1985) (nucleotide sequence of *Bacillus subtilis* levansucrase gene), Pen et al., (1992) (production of transgenic plants that express *Bacillus licheniformis* α-amylase), U.S. Pat. No. 6,166,292 (low raffinose), Elliot et al., (1993) (nucleotide sequences of tomato invertase genes), Sergaard et al., (1993) (site-directed mutagenesis of barley α-amylase gene), Fisher et al., (1993) (maize endosperm starch branching enzyme II), and U.S. Pat. Nos. 6,538,181; 6,538,179; 6,538,178; 5,750,876 and 6,476,295 (starch content). The Z10 gene encoding a 10 kD zein storage protein from maize may also be used to alter the quantities of 10 kD Zein in the cells relative to other components (Kirihara et al., 1988).

Additional transgenes for use according to the invention include, but are not limited to, transgenes conferring increased intrinsic yield (e.g., eIF5A, deoxyhypusine synthase, serine carboxypeptidase, 2,4-D dioxygenase), increased nutrient use efficiency, such as nitrogen use efficiency, increased cold tolerance, increased stress resistance and increased drought tolerance (e.g., cspB, transcription factors).

II. ANTISENSE AND RNAI CONSTRUCTS

A transgene for use according to the invention may also comprise an antisense or RNAi coding sequence. Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see above) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

RNA interference (RNAi) is a process utilizing endogenous cellular pathways whereby a double stranded RNA (dsRNA) specific target gene results in the degradation of the mRNA of interest. In recent years, RNAi has been used to perform gene "knockdown" in a number of species and experimental systems, from the nematode C. elegans, to plants, to insect embryos and cells in tissue culture (Fire et al., 1998; Martinez et al., 2002; McManus and Sharp, 2002). RNAi works through an endogenous pathway including the Dicer protein complex that generates ~21-nucleotide small interfering RNAs (siRNAs) from the original dsRNA and the RNA-induced silencing complex (RISC) that uses siRNA guides to recognize and degrade the corresponding mRNAs. Only transcripts complementary to the siRNA are cleaved and degraded, and thus the knock-down of mRNA expression is usually sequence specific. One of skill in the art would routinely be able to identify portions of, for instance, an insect gene sequence, as targets for RNAi-mediated gene suppression to mediate morbidity and/or mortality in pest of interest.

III. TISSUE CULTURES

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Nutrient media is prepared as a liquid, but this may be solidified by adding the liquid to materials capable of providing a solid support. Agar is most commonly used for this purpose. Bacto™ agar (Difco-BD, Franklin Lakes, N.J.), Hazleton agar (Hazleton, Lenexa, Kans., USA), Gelrite® (Sigma, St. Louis, Mo.), PHYTAGEL (Sigma-Aldrich, St. Louis, Mo.), and GELGRO (ICN-MP Biochemicals, Irvine, Calif., USA) are specific types of solid support that are suitable for growth of plant cells in tissue culture.

Some cell types will grow and divide either in liquid suspension or on solid media. As disclosed herein, plant cells will grow in suspension or on solid medium, but regeneration of plants from suspension cultures typically requires transfer from liquid to solid media at some point in development. The type and extent of differentiation of cells in culture will be affected not only by the type of media used and by the environment, for example, pH, but also by whether media is solid or liquid.

Tissue that can be grown in a culture includes meristem cells, callus, immature embryos, hairy root cultures, and gametic cells such as microspores, pollen, sperm and egg cells. Callus may be initiated from tissue sources including, but not limited to, immature embryos, seedling apical meristems, root, leaf, microspores and the like. Those cells which are capable of proliferating as callus also are candidate recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population, for example by manual selection and culture of friable, embryogenic tissue. Manual selection techniques which can be employed to select target cells may include, e.g., assessing cell morphology and differentiation, or may use various physical or biological means. Cryopreservation also is a possible method of selecting for recipient cells.

Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components, but may differ in the composition and proportions of their ingredients depending on the particular application envisioned. For example, various cell types usually grow in more than one type of media, but will exhibit different growth rates and different morphologies, depending on the growth media. In some media, cells survive but do not divide. Various types of media suitable for culture of plant cells previously have been described. Examples of these media include, but are not limited to, the N6 medium described by Chu et al., (1975) and MS media (Murashige and Skoog, 1962).

IV. METHODS FOR GENETIC TRANSFORMATION

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by *Agrobacterium*-mediated transformation (U.S. Pat. Nos. 5,591,616 and 5,563,055; both specifically incorporated herein by reference) and by acceleration of DNA coated particles (U.S. Pat. Nos. 5,550,318; 5,538,877; and 5,538,880; each specifically incorporated herein by reference in its entirety), etc. Through the application of techniques such as these, the cells of virtually any plant species may be stably transformed, and these cells developed into transgenic plants.

A. *Agrobacterium*-Mediated Transformation

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

*Agrobacterium*-mediated transformation is most efficient in dicotyledonous plants and is the preferable method for transformation of dicots, including *Arabidopsis*, tobacco, tomato, alfalfa and potato. Indeed, while *Agrobacterium*-mediated transformation has been routinely used with dicotyledonous plants for a number of years, it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., 1997; U.S. Pat. No. 5,591,616), wheat (McCormac et al., 1998), barley (Tingay et al., 1997; McCormac et al., 1998), alfalfa (e.g., Thomas et al., 1990; McKersie et al., 1993) and maize (Ishida et al., 1996).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

B. Electroporation

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

C. Microprojectile Bombardment

Another method for delivering transforming DNA segments to plant cells in accordance with the invention is microprojectile bombardment (U.S. Pat. Nos. 5,550,318; 5,538,880; 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics® Particle Delivery System (Dupont), which can be used to propel particles coated with DNA or cells through a screen, such as a stainless steel or nylon screen (e.g., NYTEX screen; Sefar America, Depew, N.Y. USA), onto a filter surface covered with plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994), wheat (U.S. Pat. No. 5,563,055), and sorghum (Casa et al., 1993); as well as a number of dicots including tobacco (Tomes et al., 1990; Buising and Benbow, 1994), soybean (U.S. Pat. No. 5,322,783), sunflower (Knittel et al., 1994), peanut (Singsit et al., 1997), cotton (McCabe and Martinell, 1993), tomato (VanEck et al., 1995), and legumes in general (U.S. Pat. No. 5,563,055, specifically incorporated herein by reference in its entirety).

D. Other Transformation Methods

Transformation of protoplasts can be achieved using methods based on calcium phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of plants from protoplasts have been described (Toriyama et al., 1986; Yamada et al., 1986; Abdullah et al., 1986; Omirulleh et al., 1993 and U.S. Pat. No. 5,508,184). Examples of the use of direct uptake transformation of protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055). Transformation with this technique is accomplished by agitating silicon carbide fibers together with cells in a DNA solution. DNA passively enters as the cells are punctured. This technique has been used successfully with, for example, the monocot cereals maize (PCT Application WO 95/06128; (Thompson, 1995) and rice (Nagatani, 1997).

V. PRODUCTION AND CHARACTERIZATION OF STABLY TRANSFORMED PLANTS

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

A. Selection

It is believed that DNA is introduced into only a small percentage of target cells in any one experiment. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphostransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces viridochromogenes*. The use of the herbicide tolerance gene encoding phosphinothricin acetyl transferase (PAT) is referred to in DE 3642 829 A, wherein the gene is isolated from *Streptomyces viridochromogenes*. In the bacterial source organism, this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato, potato (De Block et al., 1987) *Brassica* (De Block et al., 1989) and maize (U.S. Pat. No. 5,550,318). In previous reports, some transgenic plants which expressed the resistance gene were completely resistant to commercial formulations of PPT and bialaphos in greenhouses.

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103. The best characterized mutant EPSPS gene conferring glyphosate resistance comprises amino acid changes at residues 102 and 106, although it is anticipated that other mutations will also be useful (PCT/WO97/4103).

To use the bar-bialaphos or the EPSPS-glyphosate selective system, transformed tissue is cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate will typically be preferred, it is proposed that ranges of 0.1-50 mg/l bialaphos or 0.1-50 mM glyphosate will find utility.

It further is contemplated that the herbicide DALAPON, 2,2-dichloropropionic acid, may be useful for identification of transformed cells. The enzyme 2,2-dichloropropionic acid dehalogenase (deh) inactivates the herbicidal activity of 2,2-dichloropropionic acid and therefore confers herbicidal resistance on cells or plants expressing a gene encoding the dehalogenase enzyme (Buchanan-Wollaston et al., 1992; U.S. Pat. No. 5,508,468).

Alternatively, a gene encoding anthranilate synthase, which confers resistance to certain amino acid analogs, e.g., 5-methyltryptophan or 6-methyl anthranilate, may be useful as a selectable marker gene. The use of an anthranilate synthase gene as a selectable marker was described in U.S. Pat. No. 5,508,468.

An example of a screenable marker trait is the enzyme luciferase. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. These assays are nondestructive and transformed cells may be cultured further following identification. The photon counting camera is especially valuable as it allows one to identify specific cells or groups of cells which are expressing luciferase and manipulate those in real time. Another screenable marker which may be used in a similar fashion is the gene coding for green fluorescent protein.

It further is contemplated that combinations of screenable and selectable markers will be useful for identification of transformed cells. In some cell or tissue types a selection agent, such as bialaphos or glyphosate, may either not provide enough killing activity to clearly recognize transformed cells or may cause substantial nonselective inhibition of transformants and nontransformants alike, thus causing the selection technique to not be effective. It is proposed that selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. It is proposed that combinations of selection and screening may enable one to identify transformants in a wider variety of cell and tissue types. This may be efficiently achieved using a gene fusion between a selectable marker gene and a screenable marker gene, for example, between an NPTII gene and a GFP gene.

B. Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm $CO_2$, and 25-250 microeinsteins $m^{-2} s^{-1}$ of light. Plants are preferably matured either in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plantcon™ containers (MP-ICN Biomedicals, Solon, Ohio, USA). Regenerating plants are preferably grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with $10^{-5}$ M abscisic acid and then transferred to growth regulator-free medium for germination.

C. Characterization

To confirm the presence of the exogenous DNA or "transgene(s)" in the regenerating plants, a variety of assays may be performed. Such assays include, for example, "molecular biological" assays, such as Southern and northern blotting and PCR; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

D. DNA Integration, RNA Expression and Inheritance

Genomic DNA may be isolated from cell lines or any plant parts to determine the presence of the exogenous gene through the use of techniques well known to those skilled in the art. Note, that intact sequences will not always be present, presumably due to rearrangement or deletion of sequences in the cell. The presence of DNA elements introduced through the methods of this invention may be determined, for example, by polymerase chain reaction (PCR). Using this technique, discreet fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR analysis. In addition, it is not typically possible using PCR™ techniques to determine whether transformants have exogenous genes introduced into different sites in the genome, i.e., whether transformants are of independent origin. It is contemplated that using PCR techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR, e.g., the presence of a gene, but also demonstrates integration into the genome and characterizes each individual transformant.

Whereas DNA analysis techniques may be conducted using DNA isolated from any part of a plant, RNA will only be expressed in particular cells or tissue types and hence it will be necessary to prepare RNA for analysis from these tissues. PCR techniques also may be used for detection and quantitation of RNA produced from introduced genes. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by northern blotting. This technique will demonstrate the presence of an RNA species and give information about the integrity of that RNA. The presence or absence of an RNA species also can be determined using dot or slot blot northern hybridizations. These techniques are modifications of northern blotting and will only demonstrate the presence or absence of an RNA species.

E. Gene Expression

While Southern blotting and PCR may be used to detect the gene(s) in question, they do not provide information as to whether the corresponding protein is being expressed. Expression may be evaluated by determining expression via transcript-profiling techniques such as by use of a microarray, and by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}C$-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

VI. BREEDING PLANTS OF THE INVENTION

In addition to direct transformation of a particular plant genotype with a construct prepared according to the current invention, transgenic plants may be made by crossing a plant having a selected DNA of the invention to a second plant lacking the construct. For example, a selected CT biosynthesis gene can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:
  (a) plant seeds of the first (starting line) and second (donor plant line that comprises a transgene of the invention) parent plants;
  (b) grow the seeds of the first and second parent plants into plants that bear flowers;
  (c) pollinate a flower from the first parent plant with pollen from the second parent plant; and
  (d) harvest seeds produced on the parent plant bearing the fertilized flower.

Backcrossing is herein defined as the process including the steps of:
  (a) crossing a plant of a first genotype containing a desired gene, DNA sequence or element to a plant of a second genotype lacking the desired gene, DNA sequence or element;
  (b) selecting one or more progeny plant containing the desired gene, DNA sequence or element;
  (c) crossing the progeny plant to a plant of the second genotype; and
  (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

VII. DEFINITIONS

Expression: The combination of intracellular processes, including transcription. In the case of a functional RNA sequence, such as an antisense RNA, siRNA or miroc RNA, expression may involve transcription and processing of the functional RNA. In the case of a polypeptide coding sequence expression includes transcription and translation to produce a polypeptide.

Expression Cassette: A transgene operably linked to nucleic acid sequences that control expression of the transgene in a cell. Expression control, sequences include but are not limited to promoters, enhancers, introns, terminators and internal ribosome entry sites.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found In this respect, the sequence may be native to the host genome, but be rearranged with respect to other genetic sequences within the host sequence. For example, a regulatory sequence may be heterologous in that it is linked to a different coding sequence relative to the native regulatory sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an $R_0$ transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

$R_0$ transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce into a plant genome by genetic transformation.

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell the DNA complement of which has been altered by the introduction of an exogenous DNA molecule into that cell.

Transgene: A segment of DNA which has been incorporated into a host genome or is capable of autonomous replication in a host cell and is capable of causing the expression of one or more RNAs and/or polypeptides. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic event: A transgenic "event" is produced by transformation of the genome of a plant with a heterologous DNA construct, including a construct that comprises a plurality of transgenes in accordance with the invention. The term "event" refers to the original transformant and includes any progeny that inherit the event, such as by sexual outcrossing. Through standard plant breeding, it is understood that one of skill in the art can introduce a given transformation event into any other genetic background that is sexually compatible with a starting plant comprising the event.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule capable of replication in a host cell and/or to which another DNA segment can be operatively linked so as to bring about replication of the attached segment. A plasmid is an exemplary vector.

VIII. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Construction of Vectors with Multiple Expression Cassettes

Figure 1B:
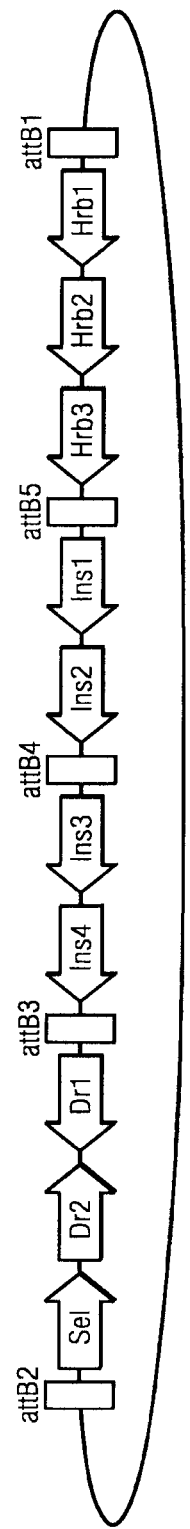

Vectors were constructed comprising either 6 or 10 expression cassettes (and 6 or 10 distinct genes). Table 1 illustrates the traits conferred by each of the transgenes in the multi-transgene vectors. Hrb1, Hrb2 and Hrb3; represent herbicide tolerance genes, Dr1 and Dr2 represent drought resistance genes; Ins1, Ins2, Ins3 and Ins4 represent insect resistance genes; and Sel represents a selectable marker gene. Also shown in Table 1 are the expression control sequences, promoter, intron and terminator that were included in each vector. Table 2 shows the number of times each promoter, intron and terminator sequence were repeated in the 10 gene construct. For construction of the multi-transgene vectors individual blocks of expression cassette sequences were cloned into a parent vector and the GATEWAY™ recombinase system was used to generate the fully formed multiple gene vector. The GATEWAY™ recombination reaction was used to directly transform *Agro-* bacterium. Bacterial colonies were screened to identify one which contained the fully formed 10 gene insert. A schematic representation of the binary T-DNA vector used for recombination and the final T-DNA vector including the ~32 KB, 10 gene insertion is shown as FIG. 1.

TABLE 1

Expression cassettes on the 10 gene vector

| Trait | Cassette (promoter/intron/gene/terminator) |
|---|---|
| Herbicide Tolerance* | ePCISV/Ract1/Hrb1/Hsp17 |
| Herbicide Tolerance* | TubA/TubA/Hrb2/TubA |
| Herbicide Tolerance* | eFMV/Sus1/Hrb3/Ara5 |
| Insect Resistance (below-ground) | e35S/Hsp70/Ins1/35S |
| Insect Resistance (below-ground) | e35S/Ract1/Ins2/Hsp17 |
| Insect Resistance (above-ground) | e35S/Ract1/Ins3/Hsp17 |
| Insect Resistance (above-ground) | FMV/Hsp70/Ins4/nos |
| Drought Tolerance* | Ract1/Ract1/Dr1/Tr7 |
| Drought Tolerance* | TubA/TubA/Dr2/TubA |
| Selectable Marker* | 35S/Sel/nos |

* = expression cassettes in the 6 gene vector.

TABLE 2

Repetition of control sequences in the 10 gene vector

| Control element | Number of repeats |
|---|---|
| 35S promoter | 4 |
| Os.Act intron | 4 |
| Hsp17 terminator | 3 |
| Hsp70 intron | 2 |
| Nos terminator | 2 |
| FMV promoter | 2 |
| TubA promoter | 2 |
| TubA intron | 2 |
| TubA terminator | 2 |
| Unique elements | 6 |

Example 2

Transformation of Plant Cells

*Agrobacterium* comprising the 10 and 6 gene vectors were used for transformation of maize immature embryos. Transformation efficiency and quality (percent single copy, backbone free sequence) was assess for the 6 and 10 gene vectors and compared to a control, 2 gene, transformation. Results of these analyses are shown in Table 3. Most transgenic events expressed all transgenes.

TABLE 3

Transformation Efficiency

| Stack | T-DNA Size (kb) | Explants | Events | TF (%) | % single copy backbone free |
|---|---|---|---|---|---|
| 2 gene | 6.6 | 440 | 79 | 18.0 | 65.8 |
| 6 gene | 17 | 440 | 69 | 15.7 | 39.1 |
| 10 gene | 32 | 440 | 20 | 4.5 | 55.0 |

Results of the transformation analysis demonstrated that transformation efficiency (TF) decreases as the number of genes in the transformation vector increased. Surprisingly, however, the 10 gene vector demonstrated enhanced transformation quality relative to the 6 gene vector and generated a significantly greater portion of single copy, backbone free inserts.

Example 3

Characterization of Transformed Plant Cells

Figure 2:
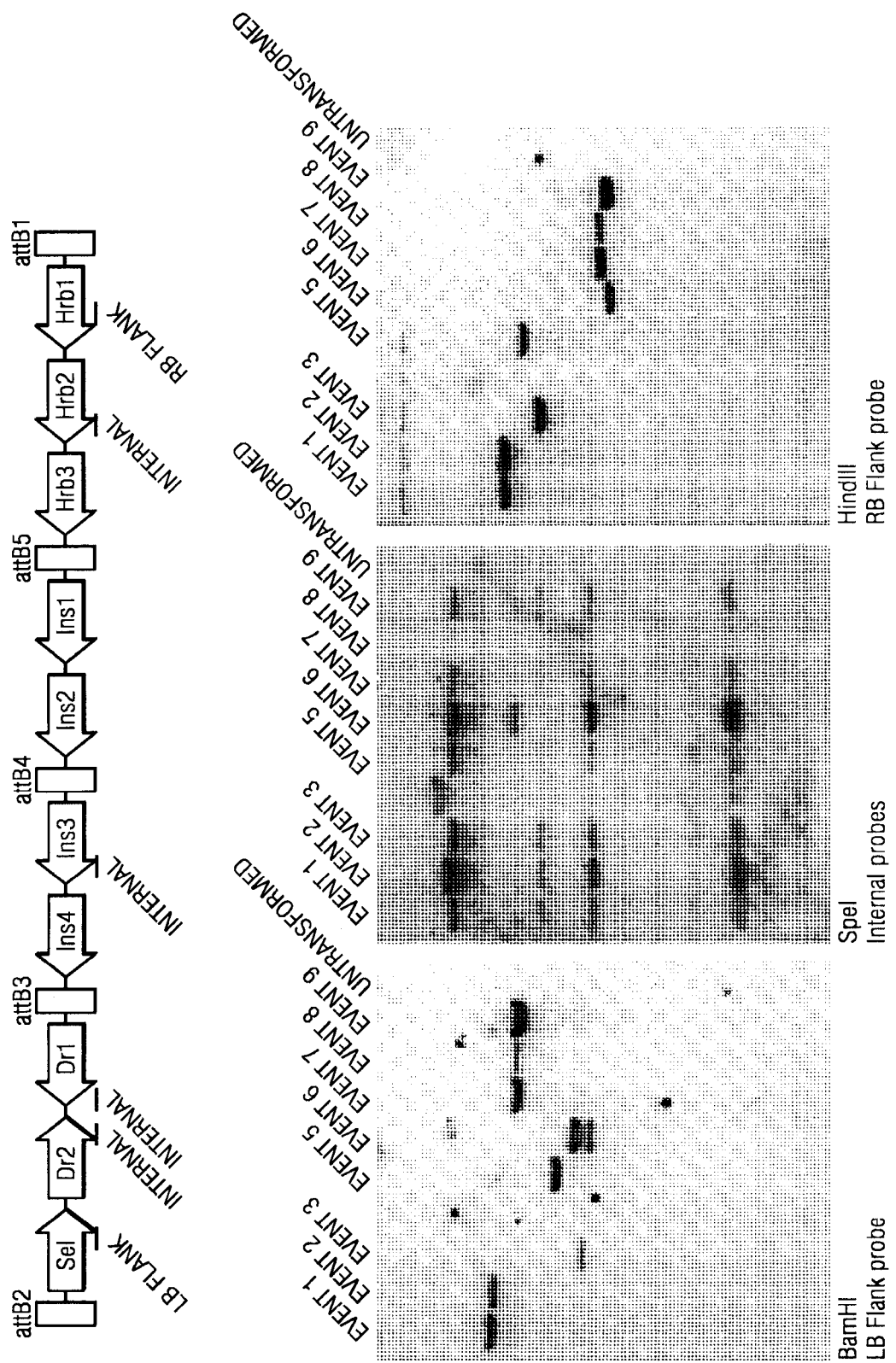
FIG. 2: A Sothern blot analysis of the plant lines transformed with the 10 gene vector.
Figure 3:
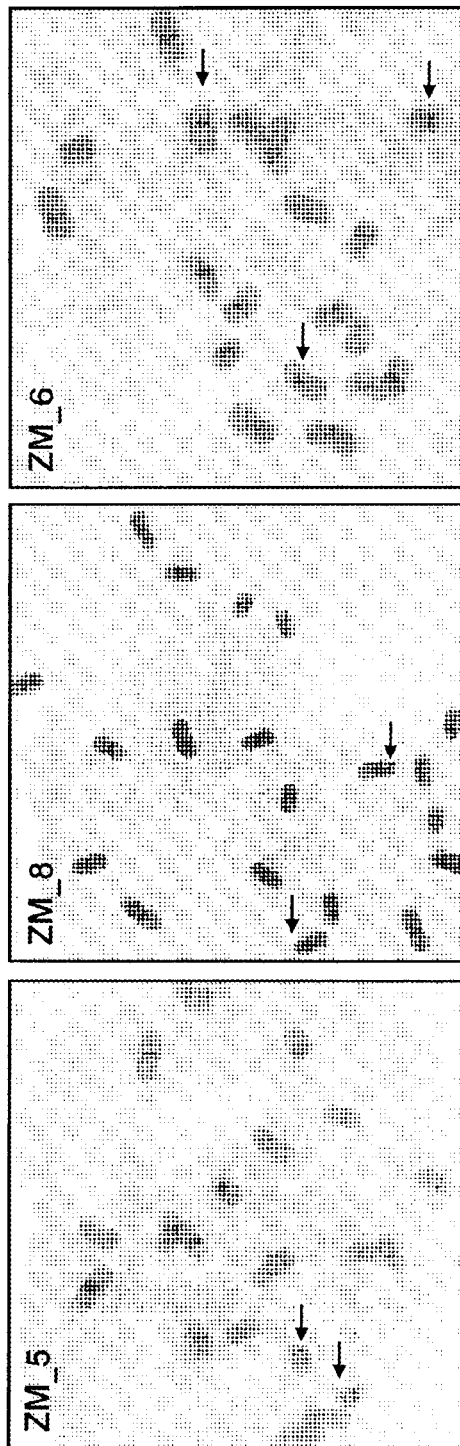
FIG. 3: FISH analysis of the chromosomes from three lines transformed with the 10 gene vector.

Transgenic events comprising the 10 gene vector were next subjected to Southern blot analysis to determine whether the transformation events comprised the intact 10 gene insertion. Results of the analysis from 9 events are shown in FIG. 2. Results of the analysis demonstrate that most events contained one, intact T-DNA insert. These results were further confirmed by FISH analysis of the three events shown in FIG. 3.

The 10 gene transformation events were next characterized for expression of the various transgenes. Table 4 shows the relative RNA expression from each of the transgenes compared to control expression vectors. In the case of Dr1 and Dr2, expression was compared to expression in a line comprising a transformation event of two transgenes (Dr1 and Dr2). Likewise for Ins1 and Ins2 expression was compared to expression in a line comprising a transformation event of two transgenes (Ins1 and Ins2). In the case of Hrb1, Hrb2 and Hrb3, expression was compared to expression in a line comprising a transformation event of three transgenes (Hrb1, Hrb2 and Hrb3). The far right two columns show absolute RNA levels as no control levels were obtained.

Figure 4:
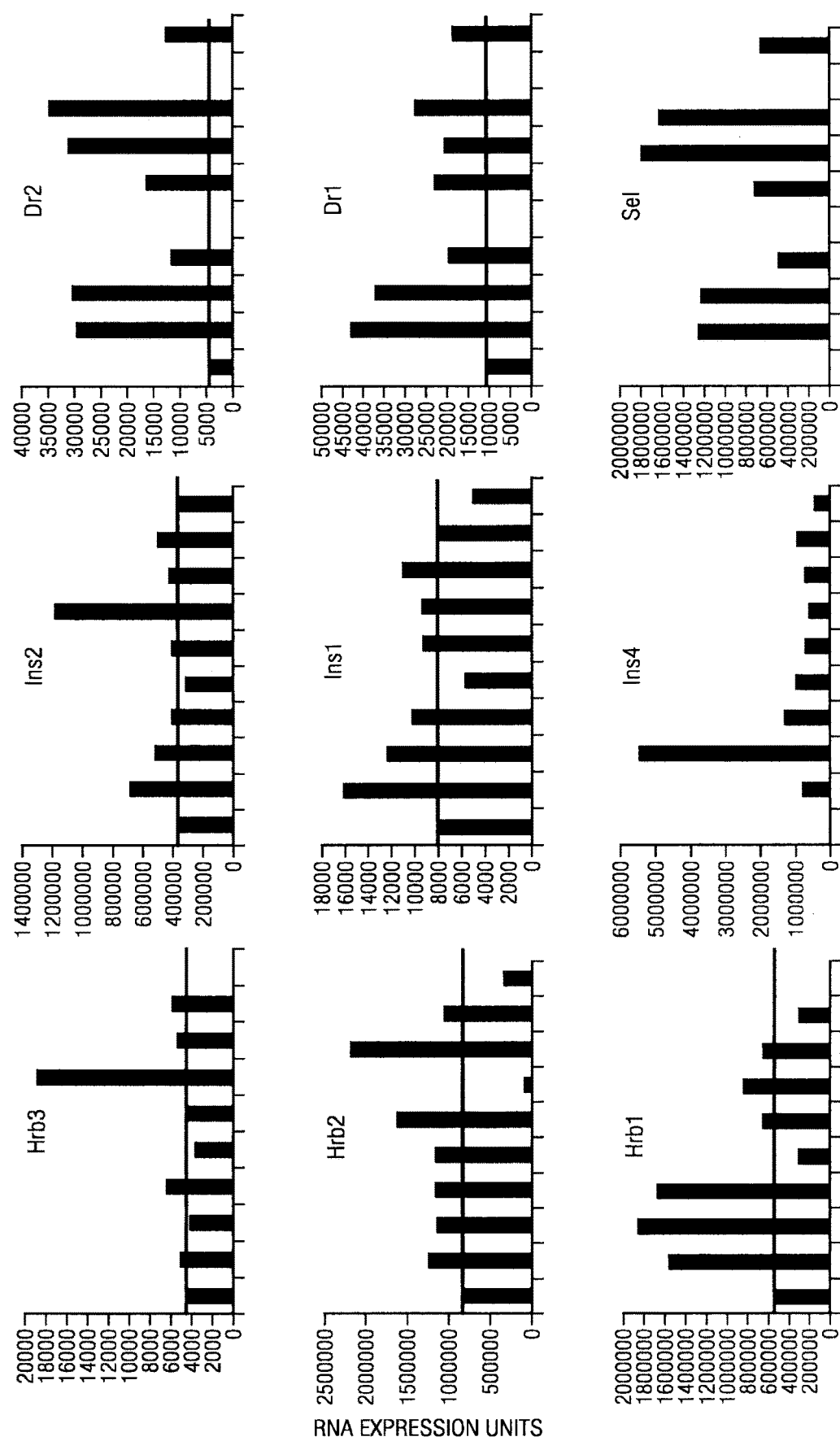
FIG. 4: Graphs illustrate RNA expression from various genes in 10 gene vector transformed lines. Horizontal lines indict the level of control expression from genes not comprised in the 10 gene system.

RNA expression results for individual transformants were also plotted on a graph as shown in FIG. 4. In each case the horizontal line indicates the level of expression from plants transformed with control vectors described above that did not comprise the 10 gene stack.

TABLE 4

Relative RNA expression from 10 gene transformation events

| | | Percent RNA Expression Compared to Control | | | | | | | Relative Expression | |
|---|---|---|---|---|---|---|---|---|---|---|
| Event | No | Dr2 | Dr1 | Ins 1 | Ins2 | Hrb3 | Hrb2 | Hrb1 | NptII | Ins4 |
| ZM_1 | 17 | 618 | 393 | 198 | 190 | 107 | 148 | 286 | 1271991 | 865519 |
| ZM_2 | 14 | 632 | 335 | 151 | 141 | 91 | 134 | 339 | 1237445 | 5554635 |
| ZM_3 | 10 | 237 | 176 | 124 | 110 | 141 | 137 | 306 | 497080 | 1354311 |
| ZM_4 | 6 | * | * | 60 | 85 | 85 | 129 | 75 | * | 1034073 |
| ZM_5 | 10 | 500 | 265 | 100 | 106 | 100 | 180 | 164 | 727638 | 771678 |
| ZM_6 | 7 | 962 | 237 | 101 | 311 | 447 | 10 | 211 | 1808399 | 619265 |
| ZM_7 | 5 | 1080 | 319 | 120 | 112 | 125 | 241 | 164 | 1642431 | 764004 |
| ZM_8 | 6 | 392 | 220 | 54 | 90 | 20763 | 38 | 0 | 670331 | 499139 |

* = Not tested.

Expression from the 10 gene transformation events was further analyzed to determine the relative protein expression levels. Results of the protein expression analysis are shown in Table 5. In the case of Hrb1, Hrb2 and Hrb3, expression was compared to expression in a line comprising a transformation event of three transgenes (Hrb1, Hrb2 and Hrb3). For Ins1 expression was compared to expression in a line comprising a transformation event of two transgenes (Ins1 and Ins2).

TABLE 5

Relative protein expression from 10 gene transformation events

| Event | N | Percent Protein Compared to Control | | | | Protein (ppm/Fresh wt) | | Percent Ins2 compared to control* |
| --- | --- | --- | --- | --- | --- | --- | --- | --- |
| | | Ins2 | Hrb3 | Hrb2 | Hrb1 | Ins4 | Ins3 | |
| ZM_1 | 10 | 137 | 146 | 86 | 84 | 11.76 | 0.43 | 43 |
| ZM_2 | 10 | 179 | 200 | 82 | 81 | 42.07 | 0.60 | 56 |
| ZM_3 | 10 | 226 | 131 | 66 | 69 | 8.97 | 0.45 | 83 |
| ZM_4 | 7 | 221 | 131 | 66 | 64 | 11.17 | 0.42 | 69 |
| ZM_5 | 10 | 175 | 130 | 77 | 77 | 10.42 | 0.47 | 55 |
| ZM_6 | 7 | 581 | 404 | 6 | 70 | 7.22 | 0.38 | 182 |
| ZM_7 | 5 | 328 | 159 | 87 | 91 | 12.50 | 0.53 | 103 |
| ZM_9 | 8 | 268 | 132 | 78 | 56 | 10.45 | 0.47 | 84 |
| ZM_8 | 6 | 318 | 295 | 30 | ND | 7.53 | 0.49 | 100 |

*Expression was compared to expression in a line comprising a transformation event of a single Ins 2 transgene.

Example 4

Analysis of Traits Conferred by Transgenes in the 10 Gene Transformation Events

Figure 5:
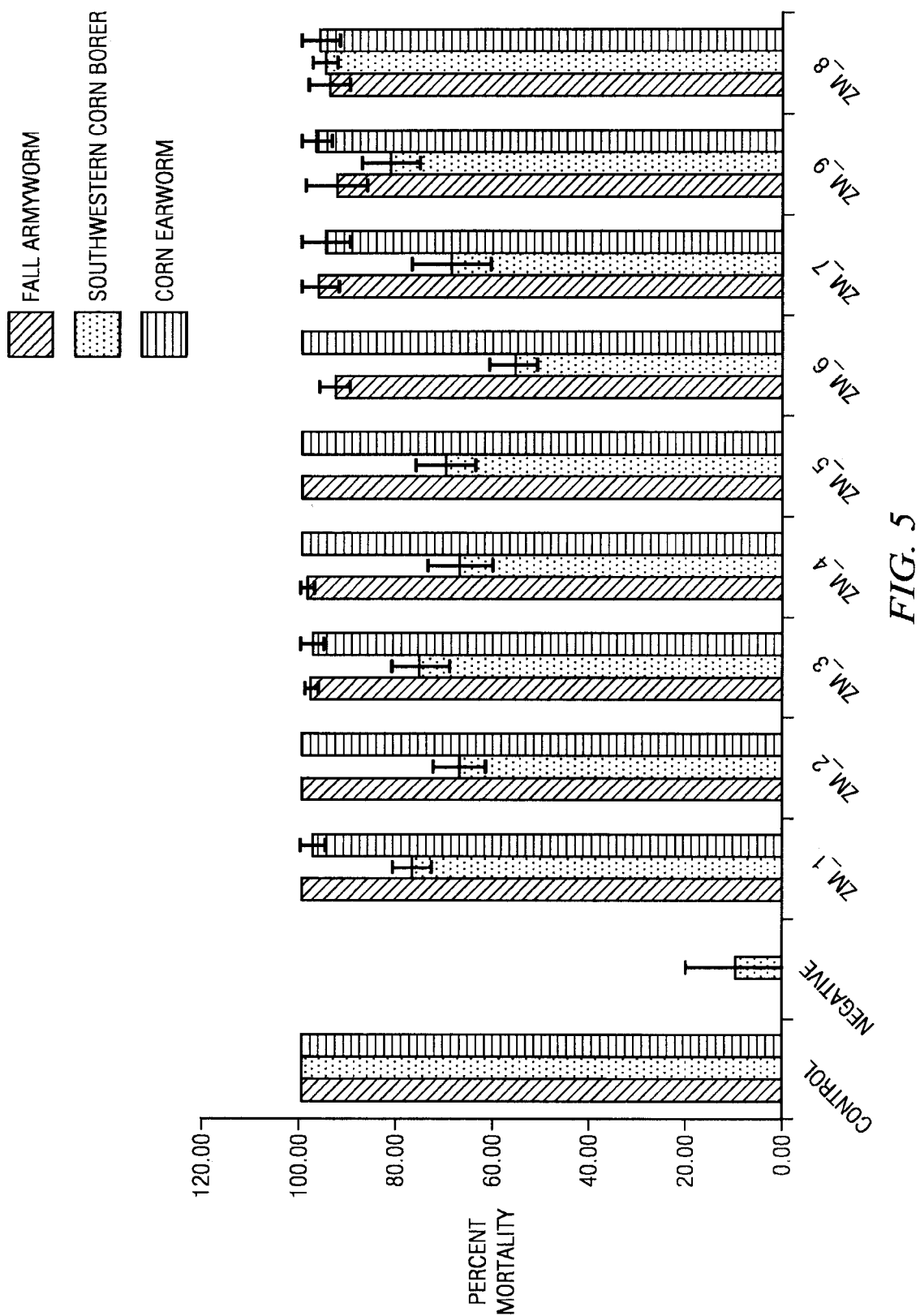
FIG. 5: Graphs indicate pest mortality when exposed to plants transformed with the 10 gene vector compared to control plants.
Figure 6:
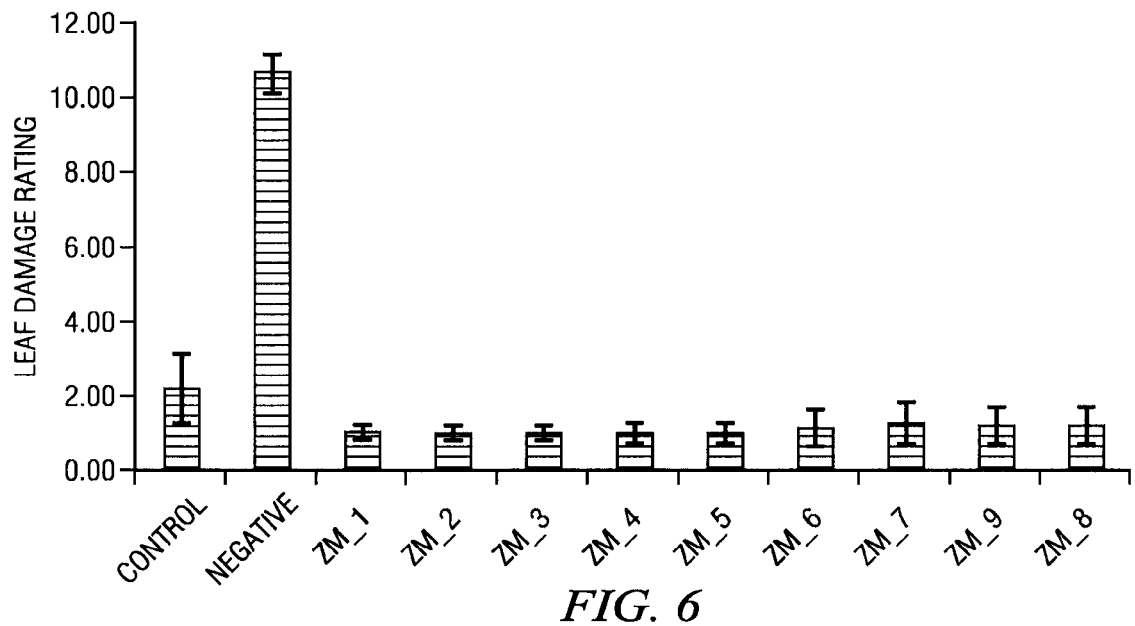
FIG. 6: Graphs indicate leaf damage in plants transformed with the 10 gene vector exposed to pests as compared to control plants.

Studies were conducted to determine whether expression from the genes in the 10 gene transformation events was sufficient to confer traits of agronomic interest to transformed plants. In a first study, transformed plants were tested for their ability to destroy three types of above ground pests. Results shown in FIG. 5 demonstrate that 10 gene transformed plants were able to destroy the three above-ground pests at a similar rate compared to plants expressing the same genes not comprised in the 10 gene system. Leaf damage was also assessed in the plants and results shown in FIG. 6 demonstrate that the 10 gene transformation events exhibited similar or less leaf damage as compared to plants expressing the same genes not comprised in the 10 gene system. In each case, "control" indicates results from a plant line transformed with a two transgene vector (encoding the Ins3 and Ins4 transgenes).

Figure 7:
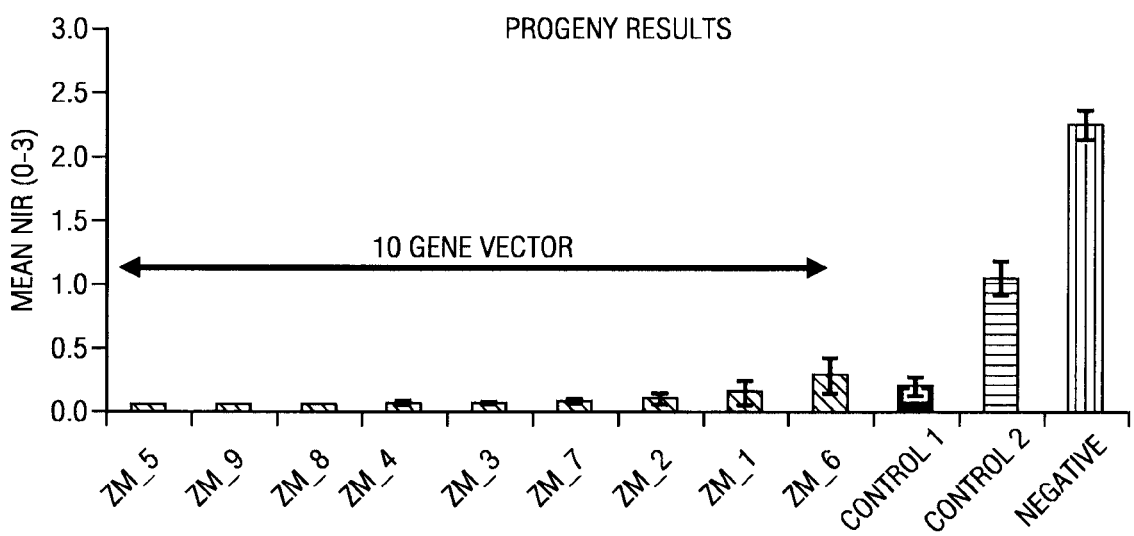
FIG. 7: Graphs indicate root damage in plants transformed with the 10 gene vector exposed to pests as compared to control plants.

Similar studies were undertaken to determine whether expression of insert resistance genes in the 10 gene transformation events were able to protect roots from damage due to *Coleoptera* pests. The graph in FIG. 7 demonstrated that genes expressed in the 10 gene transformation events protected the plants at least as well or better than identical genes expressed in plants that did not have the 10 gene stack. Control 1 is a plant line transformed with a two transgene vector (encoding the Ins1 and Ins2 transgenes). Control 2 is a plant line transformed with a single transgene vector (encoding the Ins2 transgene).

What is claimed is:

1. A method for expressing a plurality of transgenes in a transgenic plant comprising:
   expressing said plurality of transgenes in the plant, wherein the plurality of transgenes comprises at least 8 transgenes,
   wherein the plurality of transgenes are comprised in a single locus of the plant,
   wherein the plurality of transgenes are operably linked to promoter sequences, and
   wherein the at least 8 transgenes are expressed at levels at least as high as levels of the same transgenes in one or more otherwise isogenic plants, said otherwise isogenic plants not having the at least 8 transgenes comprised in a single locus.

2. The method of claim 1, wherein the expression of at least one transgene of the plurality of transgenes in said transgenic plant is enhanced relative to an otherwise isogenic plant comprising a locus comprising fewer than said plurality of transgenes.

3. The method of claim 1, wherein the expression of at least two transgenes in said transgenic plant is enhanced relative to an otherwise isogenic plant comprising a locus comprising fewer than said of plurality transgenes.

4. The method of claim 1, wherein at least one transgene confers a trait of agronomic interest.

5. The method of claim 4, wherein the trait of agronomic interest is selected from the group consisting of herbicide tolerance, drought resistance, insect resistance, fungus resistance, virus resistance, bacteria resistance, male sterility, cold tolerance, salt tolerance, increased yield, enhanced oil composition, increased oil content, enhanced nutrient use efficiency and altered amino acid content.

6. The method of claim 1, wherein said locus comprises at least one transgene that confers herbicide tolerance, at least one transgene that confers insect resistance and at least one transgene that confers drought tolerance.

7. The method of claim 6, wherein said locus comprises at least two transgenes that confer herbicide tolerance, at least two transgenes that confer insect resistance and at least two transgenes that confer drought tolerance.

8. The method of claim 1, wherein said locus comprises at least one transgene that confers above-ground insect resistance and at least one transgene that confers below-ground insect resistance.

9. The method of claim 1, wherein said locus comprises at least 9 or at least 10 transgenes.

10. The method of claim 1, wherein said single locus is a single transformation event.

11. The method of claim 1, wherein said plant is selected from the group consisting of wheat, maize, rye, rice, corn, oat, barley, turfgrass, sorghum, millet, sugarcane, tobacco, tomato, potato, soybean, cotton, canola, sunflower and alfalfa.

12. A method for enhancing the expression of a transgene in a transgenic plant comprising
expressing the transgene as a member of a plurality of transgenes within a single locus, wherein the expression of the transgene is enhanced relative to the expression of the transgene in an otherwise isogenic plant in which the transgene is not expressed as a member of said plurality of transgenes arranged in tandem within said single locus, wherein the plurality of transgenes comprises at least 8 transgenes.

13. The method of claim 12, wherein each member of the plurality of transgenes is operably linked to a separate promoter element.

14. The method of claim 12, wherein the expression of at least two transgenes is enhanced relative to the expression of the two transgenes in an otherwise isogenic plant in which the two transgenes are not expressed as members of said plurality of transgenes arranged in tandem within said single locus.

15. The method of claim 12, wherein said transgene confers a trait of agronomic interest.

16. The method of claim 15, wherein the trait of agronomic interest is selected from the group consisting of herbicide tolerance, drought resistance, insect resistance, fungus resistance, virus resistance, bacteria resistance, male sterility, cold tolerance, salt tolerance, increased yield, enhanced oil composition, increased oil content, enhanced nutrient use efficiency and altered amino acid content.

17. The method of claim 12, wherein said locus comprises at least one transgene that confers herbicide tolerance, at least one transgene that confers insect resistance and at least one transgene that confers drought tolerance.

18. The method of claim 17, wherein said locus comprises at least two transgenes that confer herbicide tolerance, at least two transgenes that confer insect resistance and at least two transgenes that confer drought tolerance.

19. The method of claim 12, wherein said locus comprises at least one transgene that confers above-ground insect resistance and at least one transgene that confers below-ground insect resistance.

20. The method of claim 12, wherein said plant is selected from the group consisting of wheat, maize, rye, rice, corn, oat, barley, turfgrass, sorghum, millet, sugarcane, tobacco, tomato, potato, soybean, cotton, canola, sunflower and alfalfa.

21. The method of claim 12, wherein the locus comprises at least 9 or at least 10 transgenes.

22. The method of claim 12, wherein said single locus is a single transformation event.

* * * * *